US011607224B2

(12) United States Patent
Valentine, Jr. et al.

(10) Patent No.: US 11,607,224 B2
(45) Date of Patent: Mar. 21, 2023

(54) SYSTEMS AND METHODS FOR POWERED SURGICAL CIRCULAR STAPLING INSTRUMENT ROTATION ADJUSTMENT

(71) Applicant: Covidien LP, Mansfield, MA (US)

(72) Inventors: David E. Valentine, Jr., Hamden, CT (US); Charles R. Kollar, Washington, DC (US); Alexander J. Hart, Tolland, CT (US); Justin Williams, Southbury, CT (US); Haley E. Strassner, Hamden, CT (US); James P. Delbo, Danville, PA (US)

(73) Assignee: COVIDEN LP, Mansfield, MA (US)

( * ) Notice: Subject to any disclaimer, the term of this patent is extended or adjusted under 35 U.S.C. 154(b) by 122 days.

(21) Appl. No.: 17/322,988

(22) Filed: May 18, 2021

(65) Prior Publication Data

US 2022/0015765 A1 Jan. 20, 2022

Related U.S. Application Data

(60) Provisional application No. 63/052,583, filed on Jul. 16, 2020.

(51) Int. Cl.
*A61B 17/115* (2006.01)
*A61B 90/00* (2016.01)
*A61B 17/00* (2006.01)

(52) U.S. Cl.
CPC .......... *A61B 17/1155* (2013.01); *A61B 90/06* (2016.02); *A61B 90/08* (2016.02);
(Continued)

(58) Field of Classification Search
CPC ...... A61B 17/1155; A61B 90/06; A61B 90/08
See application file for complete search history.

(56) References Cited

U.S. PATENT DOCUMENTS 10,085,744 B2 10/2018 Williams et al.
2016/0310134 A1* 10/2016 Contini ............ A61B 17/07207
(Continued)

FOREIGN PATENT DOCUMENTS

EP 3243450 A1 11/2017
EP 3412225 A1 12/2018
WO 2016171947 A1 10/2016

OTHER PUBLICATIONS

Extended European Search Report dated Dec. 14, 2021 corresponding to counterpart Patent Application EP 21185532.5.

*Primary Examiner* — Nathaniel C Chukwurah
(74) *Attorney, Agent, or Firm* — Carter, DeLuca & Farrell, LLP

(57) ABSTRACT

A method for powered surgical stapling instrument rotation adjustment includes measuring a change in position of a first motor shaft of the surgical stapling instrument relative to a stored rotation verification position of the first motor shaft resulting from manual rotation of an adapter assembly of the surgical stapling instrument in relation to a handle assembly of the surgical stapling instrument, determining a distance traveled by a first drive assembly of the adapter assembly of the surgical stapling instrument resulting from the change in position of the first motor shaft, comparing the determined distance traveled to a first stored rotation verification position of the first motor shaft, determining if the compared distance falls into a predetermined acceptable range of rotation positions, and adjusting the position of the drive shaft if the compared distance is not within the predetermined range.

20 Claims, 6 Drawing Sheets

(52) U.S. Cl.
CPC ............ *A61B 2017/00199* (2013.01); *A61B 2017/00367* (2013.01); *A61B 2090/061* (2016.02); *A61B 2090/0811* (2016.02)

(56) References Cited

U.S. PATENT DOCUMENTS

| | | |
|---|---|---|
| 2018/0353186 A1* | 12/2018 | Mozdzierz ........... A61B 17/072 |
| 2019/0343517 A1 | 11/2019 | Zemlok et al. |
| 2020/0015820 A1 | 1/2020 | Contini et al. |

\* cited by examiner

SYSTEMS AND METHODS FOR POWERED SURGICAL CIRCULAR STAPLING INSTRUMENT ROTATION ADJUSTMENT

CROSS-REFERENCE TO RELATED APPLICATIONS

The present application claims the benefit of and priority to U.S. Provisional Patent Application Ser. No. 63/052,583, filed on Jul. 16, 2020, the entire content of which being hereby incorporated by reference.

FIELD

The disclosure relates generally to surgical stapling instruments, and more particularly, to systems and methods for powered surgical circular stapling instrument rotation adjustment.

BACKGROUND

Anastomosis is the surgical joining of separate hollow organ sections. Typically, an anastomosis procedure follows surgery in which a diseased or defective section of an organ is removed, and the remaining end sections of the organ are joined via a surgical stapling instrument. Depending on the desired anastomosis procedure, the end sections may be joined by circular or side-to-side organ reconstruction methods, for instance.

In a circular anastomosis procedure, the remaining end sections of the organ are joined by means of a surgical stapling instrument which drives a circular array of staples through the end sections and simultaneously cores any tissue interior of the driven circular array of staples to free a tubular passage within the organ. Typically, these surgical stapling instruments include a reload assembly, an adapter assembly, and a handle assembly. The reload assembly is separable from the adapter assembly and is disposable. In order to provide cost savings, the adapter assembly is removable from the handle assembly to facilitate sterilization and cleaning of the adapter assembly.

In known powered stapling instruments, the handle assembly includes motors that are coupled to drive assemblies within the adapter assembly via gear assemblies such that actuation of the motors causes axial movement of the drive assemblies to affect various operations of the stapling instrument, i.e., clamping, firing, and cutting. The relative positions of the motors in relation to the drive assemblies is determined to calculate the required actuation strokes to properly treat tissue.

In some powered instruments, the adapter assembly is coupled to the handle assembly by a manual rotation knob that allows the adapter assembly to rotate in relation to the handle assembly to facilitate repositioning of the tool assembly within a body cavity. During a surgical procedure, manual rotation of the adapter assembly in relation to the handle assembly may change the relative positions of the motors and drive assemblies and affect the required actuation stroke to properly treat the tissue.

A continuing need exists for a powered handle assembly that can identify when the surgical stapling instrument needs to be recalibrated.

SUMMARY

In accordance with the disclosure, a method for powered surgical stapling instrument rotation adjustment, including measuring a change in position of a first motor shaft of the surgical stapling instrument relative to a stored rotation verification position of the first motor shaft resulting from manual rotation of an adapter assembly of the surgical stapling instrument in relation to a handle assembly of the surgical stapling instrument, determining a distance traveled by a first drive assembly of the adapter assembly of the surgical stapling instrument resulting from the change in position of the first motor shaft, comparing the determined distance traveled to a first stored rotation verification position of the first motor shaft, determining if the compared distance falls into a predetermined acceptable range of rotation positions, and adjusting the position of the drive shaft if the compared distance is not within the predetermined range.

In an aspect, the method may further include determining a rotation compensation value based on a difference between the predetermined rotation position and the compared distance. Adjusting the position of the drive shaft may be based on the rotation compensation value.

In another aspect, the method may further include determining a distance traveled by a second drive assembly.

In yet another aspect, the determined distance traveled by the second drive assembly may be based on a ratiometric relationship between a first gear ratio of the first drive assembly and a second gear ratio of the second drive assembly.

In an aspect, the first gear may be related to a first mode and a second gear is related to a second mode of the surgical stapling instrument.

In another aspect, determining the rotation verification position may be based on a predetermined distance to be traveled by the first drive assembly.

In yet another aspect, in a case where the first drive assembly may be not in a valid position, the method further comprises displaying a graphic warning on a display indicating an invalid rotation.

In still yet another aspect, the method may further include calculating a percent clamped based on determined distance traveled by the first drive assembly.

In still yet another aspect, the first mode may include a clamp function.

In accordance with the disclosure, surgical circular stapling instrument includes an adapter assembly, a handle assembly, a processor, and a memory. The adapter assembly includes an anvil assembly including an anvil head and an anvil center rod extending proximally from the anvil head, a reload assembly including an annular staple cartridge including a plurality of staples, a staple pusher, and a first drive assembly including a first lead screw and a first nut, configured to move through a predetermined stroke to move the anvil assembly in relation to the staple cartridge. The handle assembly including a first motor shaft, configured to advance the first drive assembly. The memory, includes instructions stored thereon, which, when executed, cause the surgical circular stapling to measure a change in position of the first motor shaft relative to a stored rotation verification position of the first motor shaft resulting from manual rotation of the adapter assembly of the surgical stapling instrument in relation to a handle assembly of the surgical stapling instrument, determine a distance traveled by a first drive assembly of the adapter assembly of the surgical stapling instrument resulting from the change in position of the first motor shaft, compare the determined distance traveled to a first stored rotation verification position of the first motor shaft, determine if the compared distance falls into a predetermined acceptable range of rotation positions, and adjust the position of the drive shaft if the compared distance is not within the predetermined range.

In another aspect, the instructions, when executed, may further cause the surgical stapling instrument to determine a rotation compensation value based on a difference between the predetermined rotation position and the compared distance. Adjusting the position of the drive shaft may be based on the rotation compensation.

In yet another aspect, the adapter assembly may further include a second drive assembly including a second lead screw and a second nut, the second lead screw movable through a predetermined stroke to move the staple pusher in relation to the staple cartridge. The handle assembly may further include a second motor including a second motor shaft, configured to advance the second drive assembly. The instructions, when executed, further cause the surgical stapling instrument to determine a distance traveled by the second drive assembly.

In still yet another aspect, the determined distance traveled by the anvil assembly may be based on a ratiometric relationship between a first gear ratio and a second gear ratio of the first drive assembly and the second drive assembly.

In still yet another aspect, the first gear is related to a first mode and a second gear may be related to a second mode of the surgical stapling instrument.

In still yet another aspect, determining the rotation verification position may be based on a predetermined distance to be traveled by the first drive assembly.

In still yet another aspect, in a case where the first drive assembly is not in a valid position, the instructions, when executed, may further cause the surgical stapling instrument to display a graphic warning on a display indicating an invalid rotation.

In still yet another aspect, in a case where the first drive assembly is not in a valid position, the instructions, when executed, may further cause the surgical stapling instrument to emit an error tone indicating an invalid rotation.

In an aspect, the instructions, when executed, may further cause the surgical stapling instrument to calculate a percent clamped based on the determined distance traveled by the first drive assembly.

In accordance with the disclosure, a non-transitory computer-readable medium storing instructions which, when executed by a processor, cause the processor to perform a method for surgical stapling instrument rotation adjustment, the method including measuring a change in position of a first motor shaft of the surgical stapling instrument relative to a stored rotation verification position of the first motor shaft resulting from manual rotation of an adapter assembly of the surgical stapling instrument in relation to a handle assembly of the surgical stapling instrument, determining a distance traveled by a first drive assembly of the adapter assembly of the surgical stapling instrument resulting from the change in position of the first motor shaft, comparing the determined distance traveled to a first stored rotation verification position of the first motor shaft, determining if the compared distance falls into a predetermined acceptable range of rotation positions, and adjusting the position of the drive shaft if the compared distance is not within the predetermined range.

BRIEF DESCRIPTION OF DRAWINGS

Systems and methods for powered circular stapler instrument rotation adjustment are disclosed herein with reference to the drawings, wherein.

DETAILED DESCRIPTION

Figure 1:
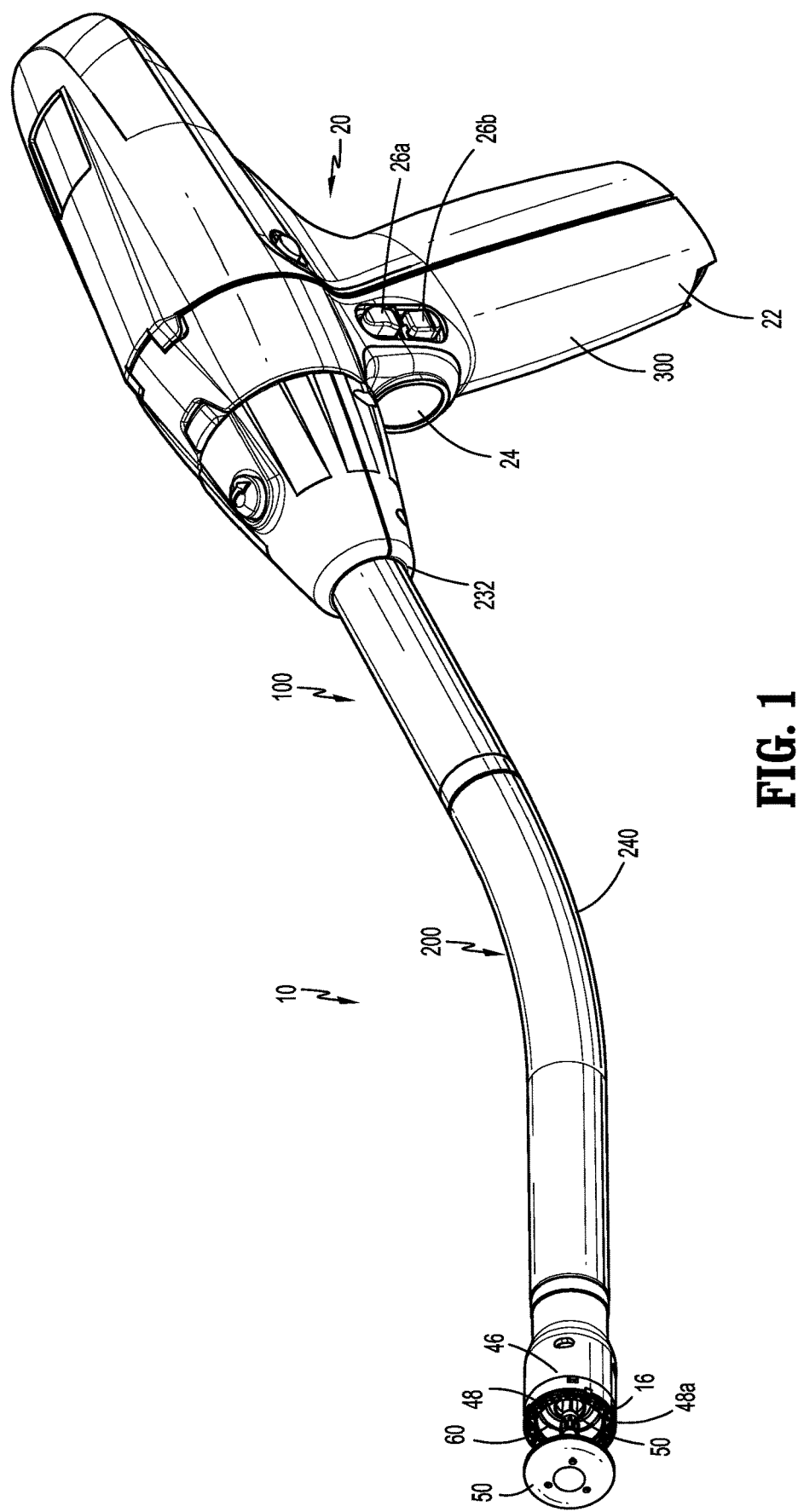
FIG. 1 is a perspective view of a surgical stapling instrument in accordance with the disclosure.

The disclosed surgical instrument will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel, including doctors, nurses, and support personnel.

The disclosed systems and methods use software to correlate the position of motors of a handle assembly of a surgical stapling instrument with the positions of drive assemblies of an adapter assembly of the surgical stapling instrument when the position of the adapter assembly in relation to the handle assembly is manually changed by a clinician. This correlation allows the surgical stapling instrument to provide a proper clamp gap, staple stroke (staple formation), and cut stroke during operation of the surgical stapling instrument.

During calibration of a surgical stapling instrument, a stroke of each of the drive assemblies of the surgical stapling instrument for performing various functions of the instrument, i.e., clamping, stapling, and cutting, is set to a predetermined distance (rotation verification position). Throughout different stages of a surgical procedure in which the surgical stapling instrument is used to treat tissue, before the surgical stapling instrument is actuated, the adapter assembly of the surgical stapling instrument may be manually rotated in relation to the handle assembly of the surgical stapling instrument by a clinician to reposition the tool assembly within a body cavity of a patient. This change in the position of the adapter assembly in relation to the handle assembly may change the relative positions of the motors within the handle assembly and the drive assemblies within the adapter assembly and thus, change the appropriate stroke of the drive assemblies required to properly actuate the tool assembly. As such, rotation of the adapter assembly in relation to the handle assembly may necessitate compensation or recalibration of the surgical stapling instrument prior to actuation of the surgical stapling instrument. This disclosure provides a method to recalibrate the motor position and the drive assembly position when the relative positions of the motors and drive assemblies have been changed as a result of manual rotation of the adapter assembly in relation to the handle assembly by a clinician prior to actuation of the surgical stapling instrument.

FIG. 1 illustrates a surgical stapling instrument shown generally as stapling instrument 10. The stapling instrument 10 is a circular stapling instrument and includes a handle assembly 20, an adapter assembly 100 that extends distally from the handle assembly 20, a reload assembly 16 that is supported on a distal portion of the adapter assembly 100, an anvil assembly 50 that is operatively coupled to the adapter assembly 100, and a controller 300 (FIG. 3) that is supported within the handle assembly 20. The reload assembly 16 supports an annular staple cartridge 48 that includes a plurality of staples (not shown). The anvil assembly 50 includes an anvil head 28 that includes a staple forming surface 29 (FIG. 2B) that defines staple forming pockets 48a (FIG. 2B) and is movable in relation to the staple cartridge 48 between open and clamped positions.

The handle assembly 20 is illustrated as a powered assembly and includes a stationary grip 22, an actuation button 24 for controlling firing of staples (not shown) from the annular staple cartridge 48 of the reload assembly 16, and approximation buttons 26a, 26b for controlling axial displacement of the anvil assembly 50 towards and away from the reload assembly 16 between the open and clamped positions. For a detailed description of the structure and function of exemplary powered handle assemblies, reference may be made to U.S. Patent Application Publication Nos. 2020/0015820 and 2019/0343517. Although the disclosure illustrates a powered assembly, it is envisioned that advantages of the disclosure, as described in detail below, are also applicable to robotically actuated surgical instruments.

The handle assembly 20 may include an electrical assembly including a strain gauge 51 (FIG. 2B) that is configured to determine if a motor 152, 154, 156 (FIG. 2C) of the stapling instrument 10 is under load or is within a predetermined load range resulting from tissue being clamped between the anvil assembly 50 and the staple cartridge 48.

Figure 2A:
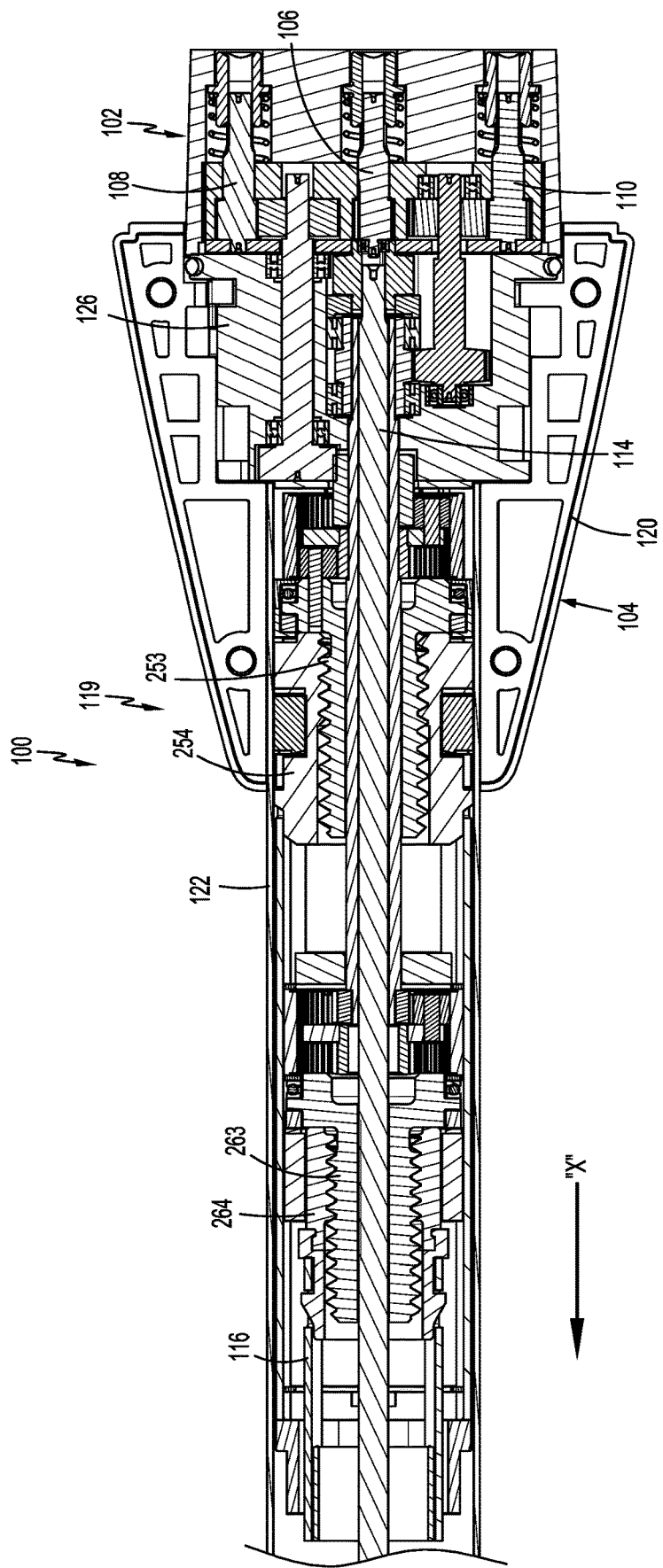
FIG. 2A is a side cross-sectional view taken through a proximal portion of an adapter assembly of the surgical stapling instrument shown in FIG. 1.
Figure 2B:
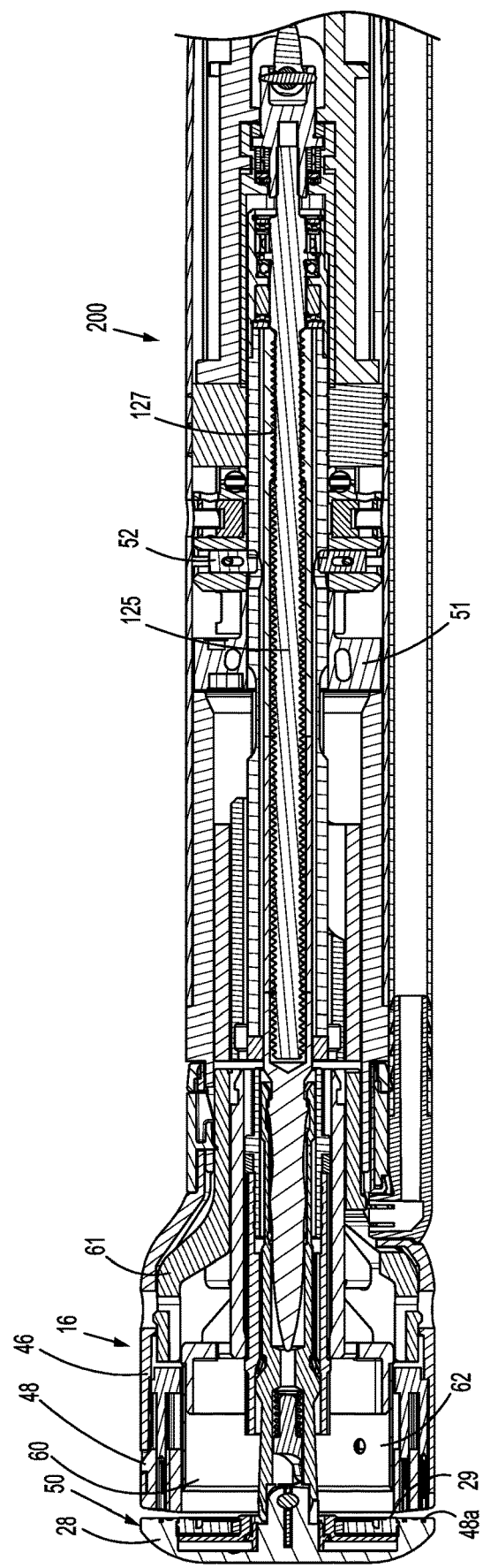
FIG. 2B is a cross-sectional view taken through the distal portion of the adapter assembly and the tool assembly of the surgical stapling instrument shown in FIG. 1.

FIG. 2A illustrates the adapter assembly 100 that includes a stationary portion 102 that is coupled to the handle assembly 20 (FIG. 1) and a rotatable portion 104 that is rotatably coupled to the stationary portion 102. The stationary portion 102 includes a first drive shaft 106, a second drive shaft 108, and a third drive shaft 110 that are coupled to drive shafts 152a, 154a, 156a of the motors 152, 154, 156 (FIG. 2C) supported within the handle assembly 20 (FIG. 1) when the adapter assembly 100 is coupled to the handle assembly 20 to control the various functions of the stapling instrument 10 (e.g., clamping, stapling, and/or cutting tissue). The drive shaft 106 in the stationary portion 102 of the adapter assembly 100 is coupled to a drive assembly 114 within the rotatable portion 104 of the adapter assembly 100 by gears to control movement of the anvil assembly 50 in relation to the staple cartridge 48 between open and clamped positions. The drive shaft 108 in the stationary portion 102 of the adapter assembly 100 is coupled to a drive assembly 119 within the rotatable portion 104 of the adapter assembly 100 by gears to control movement of a pusher assembly 61 (FIG. 2B) within the reload assembly 16 (FIG. 1) to control firing of staples from the staple cartridge 48 (FIG. 1). The drive shaft 110 in the stationary portion 102 of the adapter assembly 100 is coupled to a drive assembly 116 by gears to control cutting of tissue. Each of the drive assemblies 114, 116, 119 (FIG. 2A) includes a screw and a nut, not described in detail herein, in which the nut is driven in relation to the screw to effect longitudinal movement of the screw.

The rotatable portion 104 of the adapter assembly 100 includes a rotation knob 120 that is rotatably coupled to and rotatable about a hub portion 126 of the stationary portion 102 of the adapter assembly 100. The rotation knob 120 is coupled to an outer tube 122 of the rotatable portion 104 of the adapter assembly 100 such that manual rotation of the rotation knob 120 about a longitudinal axis "X" of the rotation knob 120 causes rotation of the rotatable portion 102 of the adapter assembly 100 in relation to the stationary portion 102 of the adapter assembly 100 and in relation to the handle assembly 20 about the longitudinal axis "X." U.S. Patent Publication No. 2018/0353186 ("'186 publication") includes a detailed description of the construction and operation of a suitable adapter assembly.

FIG. 1 illustrates the reload assembly 16, which is supported on a distal portion of the outer tube 122 of the adapter assembly 100 and includes a shell housing 46 that supports the staple cartridge 48. In aspects of the disclosure, the staple cartridge 48 defines annular rows of staple receiving pockets 48a which receive staples (not shown). In some aspects of the disclosure, the reload assembly 16 is releasably coupled to the distal portion of the tubular shaft (not shown) to facilitate the replacement of the annular staple cartridge 48 after each use to facilitate reuse of the surgical instrument 10. For a detailed description of exemplary aspects of a powered handle assembly and a releasable adapter assembly, reference may be made to U.S. Pat. No. 10,085,744.

Each of the staple receiving pockets 48a (FIG. 2B) of the staple cartridge 48 supports a staple (not shown) that can be fired from the staple cartridge 48 via actuation of the actuation button 24 of the handle assembly 20. The shell housing 46 of the reload assembly 16 defines an annular cavity 60. The annular cavity 60 supports the staple pusher 61 (FIG. 2B) and an annular knife 62 that are coupled to the drive assembly 119 (FIG. 2A) and the knife driver nut 264 of the drive assembly 116 (FIG. 2A), respectively, such that the staple pusher 61 and the annular knife 62 are movable in relation to the staple cartridge 48 to eject the staples from the staple cartridge 48 and to dissect or cut tissue positioned within an annulus defined by the staple cartridge 48. When the staples (not shown) are fired from the staple cartridge 48, the staples are driven into and formed within the staple forming pockets 29a (FIG. 2B) of the staple forming surface 29 of the anvil head 28 of the anvil assembly 50.

As described above, the first, second, and third shafts are 106, 108, and 110 of the adapter assembly 100 are coupled to the powered handle assembly 20 by motor shafts 152a, 154a, 156a that are coupled to motors 152, 154, 156 (FIG. 2C) within the handle assembly 20 by gear assemblies (not shown). Rotation of the motor shafts 152a, 154a, 156a by the motors 152, 154, 156 are controlled by the controller 300 such that the motors 152, 154, 156 move drives the shafts 106, 108, and 110 to move the drive assembly 114, the drive assembly 119, and the drive assembly 116 through predetermined strokes to move the anvil assembly 50 in relation to the staple cartridge 48 from the open to the clamped position to define a predetermined tissue gap between the anvil assembly 50 and the staple cartridge 48, to advance the pusher (not shown) within the shell housing 46 to eject staples from the staple cartridge 48, and to advance the knife carrier (not shown) within the shell housing 46 to cut tissue. The predetermined strokes are calculated from reference positions, which are based on the rotational position of the motor drive shafts 152a, 154a, 156a within the handle assembly 20.

Rotation of the adapter assembly 100 relative to the handle assembly may change the position of the drive assemblies 114, 119, 116, thus requiring the stroke to be changed. The disclosed method determines whether the adapter assembly 100 of the stapling instrument 10 has been rotated relative to the handle assembly 20 of the stapling instrument 10 by performing a series of staple calibration checks throughout the surgical procedure prior to actuation of the surgical instrument 10. The gear ratios of the gear assemblies interconnecting the motor shafts 152a, 154a, 156a to the drive assemblies 114, 116, 119 are fixed with respect to their specific functions. Therefore, the distance traveled when the stapling instrument 10 is rotated is ratiometric between the staple, clamp, and cutting functions. Using these known ratios, calibration distance differential windows (e.g., ranges) can be established for each of the rotation positions (e.g., 0°, 90°, or 180°) of the adapter assembly 100 in relation to the handle assembly 20. Each respective position may have an associated tolerance window (e.g., a range) where a normal calibration distance differential can be reported.

When the adapter assembly 100 of the stapling instrument 10 has been rotated relative to the handle assembly 20, and the disclosed rotation verification method is utilized, the position of the anvil assembly 50 relative to the staple cartridge 48 of the surgical instrument 10 will be adjusted based upon the differential window that the determined distance falls into. This verification occurs when there is no load on the surgical instrument 10. The disclosed method maintains consistency of staple formation, maintains consistent tissue gap, prevents over-compression of tissue, and lowers surgical times, reducing surgical intervention.

When the rotatable portion 104 of the adapter assembly 100 is rotated about the longitudinal axis "X" (FIG. 2A) of the rotation knob 120 in relation to the stationary portion 102 of the adapter assembly 100 to reposition the reload assembly 16 and anvil assembly 50 within a body cavity of a patient, rotation of the rotatable portion 104 of the adapter assembly 100 in relation to the handle assembly 20 changes the reference position of each of the drive assemblies 114, 116, 119 within the adapter assembly 100. As such, recalibration of the stapling instrument 10 is required before actuation of the stapling instrument 10.

Drive assembly 119 (FIG. 2A) includes a staple lead screw 253 and a staple driver nut 254 in which the staple driver nut 254 is driven in relation to the staple lead screw 253 to effect longitudinal movement of the staple lead screw 253. Drive assembly 116 (FIG. 2A) includes a knife lead screw 263 and a knife driver nut 264 in which the knife driver nut 264 is driven in relation to the knife lead screw 263 to effect longitudinal movement of the knife lead screw 263. Drive assembly 114 (FIG. 2B) includes a lead screw 125 and a nut 127 in which the nut 127 is driven in relation to the lead screw 125 to effect longitudinal movement of the lead screw 125.

Figure 3:
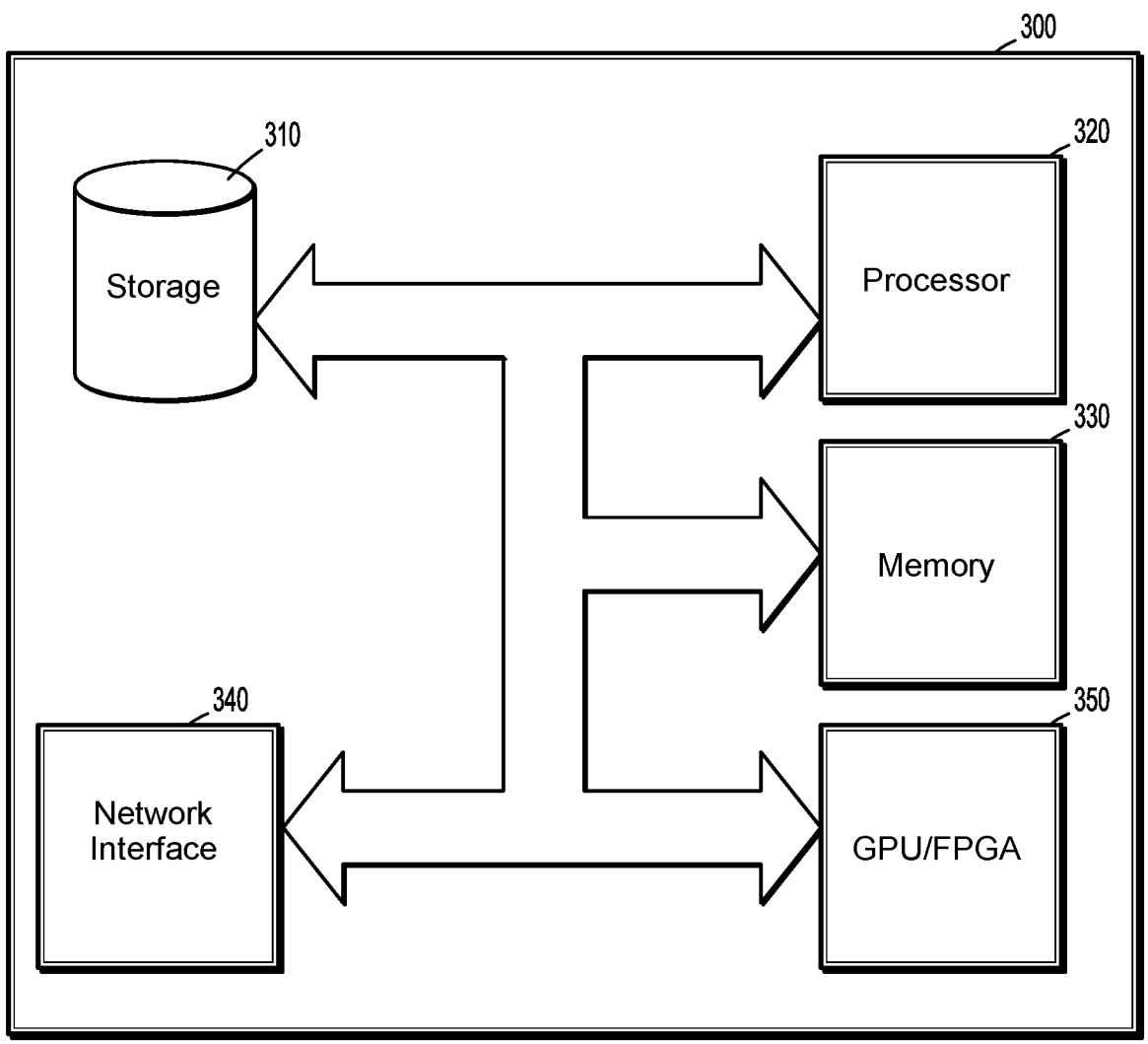
FIG. 3 is a block diagram of a controller provided in accordance with the disclosure and configured for use with the surgical system of FIG. 1.

FIG. 3 illustrates the controller 300, in accordance with the disclosure, which includes a processor 320 that is connected to a computer-readable storage medium or a memory 330. The computer-readable storage medium or memory 330 may be a volatile type memory, e.g., RAM, or a non-volatile type memory, e.g., flash media, disk media, etc. In various aspects of the disclosure, the processor 320 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memistors, chemically, or other inference calculations, as opposed to processors.

In aspects of the disclosure, the memory 330 can be random access memory, read-only memory, magnetic disk memory, solid-state memory, optical disc memory, and/or another type of memory. In some aspects of the disclosure, the memory 330 can be separate from the controller 300 and can communicate with the processor 320 through communication buses of a circuit board and/or through communication cables such as serial ATA cables or other types of cables. The memory 330 includes computer-readable instructions that are executable by the processor 320 to operate the controller 300. In other aspects of the disclosure, the controller 300 may include a network interface 340 to communicate with other computers or to a server. A storage device 310 may be used for storing data.

The controller 300 includes a plurality of sensors (not shown) configured to measure operational states of the motors 152, 154, 156. The sensors may include, for example, voltage sensors, current sensors, temperature sensors, telemetry sensors, optical sensors, and combinations thereof. The sensors may measure voltage, current, and other electrical properties of electrical energy supplied to the motors 152, 154, 156. The sensors may also measure angular velocity (e.g., rotational speed) as revolutions per minute (RPM), torque, temperature, current draw, and other operational properties of the motors 152, 154, 156. Angular velocity may be determined by measuring the rotation of the motors 152, 154, 156, or a drive shaft (not shown) coupled thereto and rotatable by the respective motor. The position of various axially movable drive shafts may also be determined by using various linear sensors disposed in or in proximity to the shafts or extrapolated from the RPM measurements. In aspects, torque may be calculated based on the regulated current draw of the motor at a constant RPM. In further aspects, the controller 300 may measure time and process the above-described values as a function of time, including integration and/or differentiation, e.g., to determine the rate of change in the measured values. The controller 300 is also configured to determine the distance traveled of various components of the adapter assembly 100 and/or the reload assembly 16 by counting revolutions of the motors 152, 154, 156.

The disclosed method may run on the controller 300 or on a user device, including, for example, on a mobile device, an IoT device, or a server system.

Figure 4:
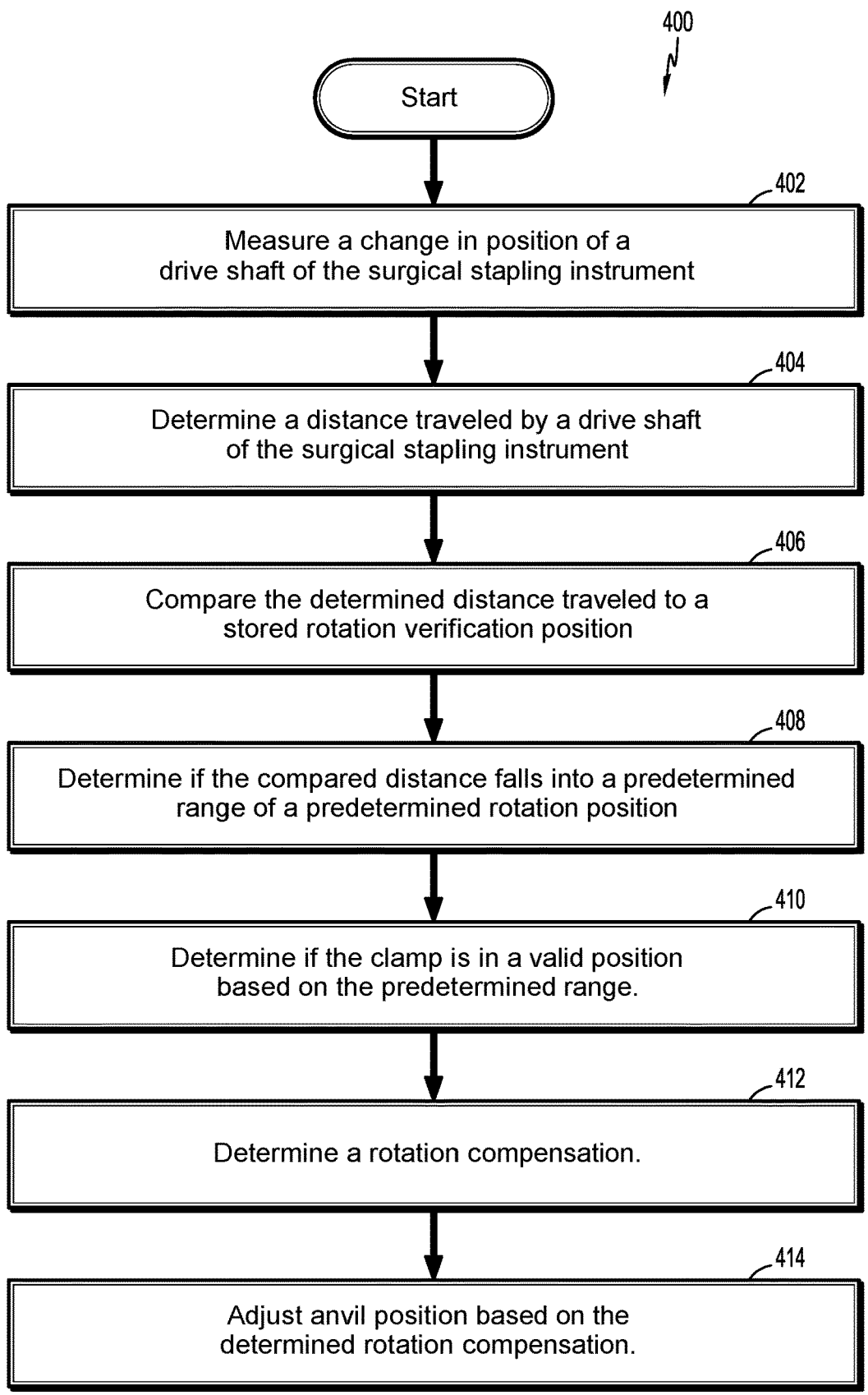
FIG. 4 is a flowchart of a method for rotation verification in accordance with the disclosure.

FIG. 4 illustrates a flow diagram of a computer-implemented method 400 for controlling the stapling instrument 10 to determine adapter rotation and allow the strokes of the drive assemblies 114, 119, and 116 to be recalibrated to ensure that the proper strokes are produced upon actuation of the stapling instrument 10. During calibration of the stapling instrument 10 (FIG. 1), a cut stroke of the drive assembly 116 is set to a predetermined distance, which may be in defined by a predetermined number of turns of the staple driver nut 264 in relation to the staple lead screw 263. A clamp stroke of the drive assembly 114 is set to a predetermined distance, which may be defined by a predetermined number of turns of the nut 127 in relation to the lead screw 125.

The clamp stroke, the staple stroke, and the cut stroke are calculated from a respective reference position of each of the drive assemblies 114, 116, 119. However, when the adapter assembly 100 is manually rotated in relation to the handle assembly 20, the reference position of each of the drive assemblies 114, 116, 119 within the adapter assembly 100 is changed and must be calibrated if outside of a predetermined range.

Figure 2C:
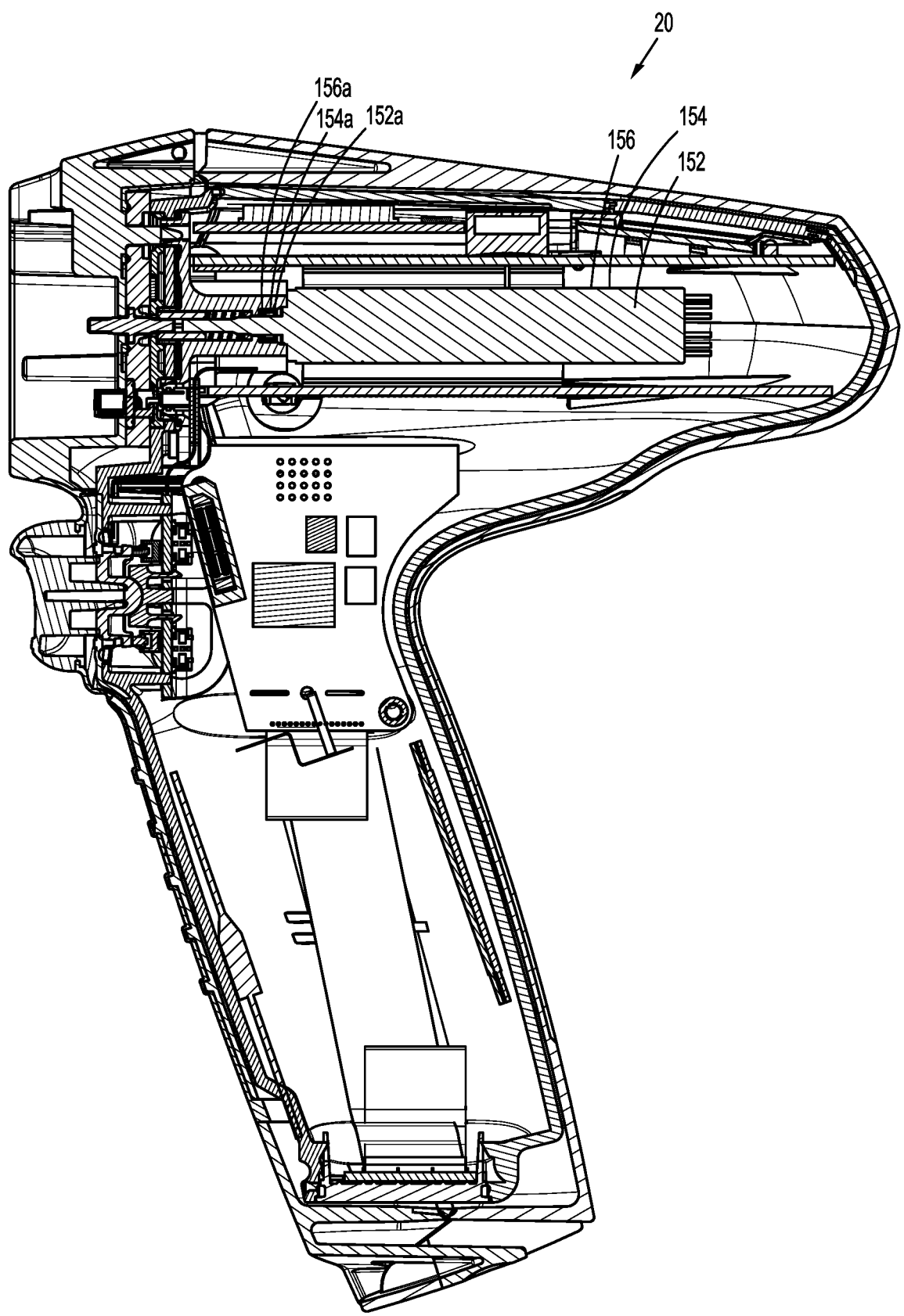
FIG. 2C is a cross-sectional view taken through the distal portion of the handle assembly of the surgical stapling instrument shown in FIG. 1.

When an adapter assembly 100 is first coupled to the handle assembly 20 with the reload assembly 16 secured to the adapter assembly, the handle assembly 20 performs calibration to determine a starting hard stop position. The controller 300 calculates the distance traveled by the motors 152, 154, 156 to determine the hard stop position. The hard stop position is a mechanical end stop position that corresponds to a spike in the current draw of the motor correlating to a torque to bottom out the knife driver nut 264 (FIG. 2A) and/or the staple driver nut 254 (FIG. 2A) on the respective lead screw 263, 253. A hard stop position is determined for each of the motors 152, 154, 156 (FIG. 2C). This is achieved during calibration of the instrument 10 by moving each of the respective drive assemblies 114 until a torque threshold of the respective motor is achieved. A rotation verification position is an initial predetermined starting point for the drive shafts 106, 108, 110 that may be set when the drive assemblies 114, 116, 119 are moved from the hard stop position a predetermined distance, e.g., at a value of a number of turns of the lead screw, e.g., five turns. This can be determined by measuring the number of turns of the motor 152, 154, 156 (FIG. 2C). The rotation verification position is stored in a memory of controller 300.

A method for operating the surgical instrument 10 is described and may be carried out prior to actuating the surgical instrument 10 after the surgical instrument 10 is properly positioned in relation to tissue to be treated, e.g., anastomosed. This method is carried out before the tissue is clamped between the staple cartridge 48 (FIG. 1) and the anvil assembly 50 and readjusts the stroke lengths of the various functions (clamping, stapling, and cutting of tissue) of the stapling instrument 10 based upon the positions of the drive assemblies 114, 116, 119 of the adapter assembly 100 which may have changed in response to manipulation of the adapter assembly 100 in relation to the handle assembly 20.

Initially, at step 402, the method determines a change in position of a respective motor shaft 152*a*, 154*b*, 156*c* (FIG. 2C) of a selected function (e.g., clamping, stapling, or cutting tissue) of the stapling instrument 10, relative to the stored rotation verification position during repositioning of the reload assembly 16 and the anvil assembly 50 within the body cavity resulting from the rotation of the adapter assembly 100 in relation to the handle assembly 20. For example, the method may determine the difference between the stored rotation verification position and change in turns of the motor shaft as the motor shaft is moved through a predetermined stroke. The rotation verification position is the position the motor shaft should be in, for example, to create a tissue gap within the predetermined range if the motor shaft is moved through the predetermined stroke. The predetermined tissue gap and the predetermined stroke are controlled by the controller 300. For example, if the clinician rotates the adapter assembly 100 relative to the handle assembly 20 between the cutting function and the stapling function, the method would measure the movement of the respective motor shafts and determine a change in position of the motor shafts relative to the rotation verification position.

Next, at step 404, the method determines a distance traveled by the motor shaft. Once this is determined, the distance traveled by the drive shaft may be calculated based on the ratiometric relationship between a first gear ratio of a first drive assembly (e.g., drive assembly 114) and a second gear ratio of the second drive assembly (e.g., drive assembly 1119). The first gear ratio is related to a first mode (e.g., a clamp function), and a second gear ratio is related to a second mode (e.g., a staple function) of the stapling instrument 10. For example, the first gear ratio may be about 2:1 (from input turns to output turns at the lead screw 125) for clamping, and the second gear ratio may be about 19:1 (from input turns to output turns at the lead screw 253) for stapling.

If the motor shaft 152*a*, 154*b*, 156*c* (FIG. 2C) is within a predetermined position to properly execute the selected function, for example, to clamp tissue or to form staples, then at step 406, the method updates the motor shaft position and stores the updated motor shaft position in memory.

To determine the distance the motor shaft has moved, the rotations of the motor that is used to rotate the motor shaft and drive the anvil assembly 50 may be measured. For example, the motor may include a predetermined number of "ticks" per rotation (e.g., 36 ticks per rotation) and an encoder may be provided for counting the ticks to identify the exact positions of the drive shafts 152*a*, 154*a*, 156*a* (FIG. 2C) as the shafts are rotated (in response to manual rotation of the adapter assembly 100 in relation to the handle assembly 20). Using this information, the positions of the drive assemblies 114, 116, and 119 can be determined to, for example, determine the position of the anvil assembly 50 in relation to the staple cartridge 48. An encoder is an electromechanical device that can measure motion or position. The encoder may use optical sensors to provide electrical signals in the form of pulse trains, which can, in turn, be translated into motion, direction, or position. Each step in position is a "tick." For example, an encoder with 360 steps would have 360 "ticks." In various aspects, the motor rotation may be determined based on a current draw of the motor of the stapling instrument 10 from the hard stop position.

Next, at step 410, the method calculates the change in distance (e.g., the number of motor ticks) of each function's motor 152, 154, 156 (FIG. 2C) from the respective hard stop position, between functions (e.g., clamp, staple, and/or cut). For example, the method may calculate the change in the number of ticks of the motor shaft when the adapter assembly 100 is rotated in relation to the handle assembly 20 after the function of clamping tissue is performed and before the stapling has begun. The movement of the different functions (e.g., clamp, staple, and/or cut) are proportional to each other based on their respective gear ratios. The gear ratios are fixed with respect to their specific functions. Therefore, the distance traveled by the respective motor shaft when the stapling instrument 10 is rotated is ratiometric (i.e., directly proportional) between clamping tissue and stapling tissue (or stapling and cutting). Based on this ratio, a predetermined range (e.g., a calibration distance differential window) may be used for each of the rotation positions (e.g., 0°, 90°, or 180°).

Next, at step 412, the method compares the determined distance traveled by the respective motor shafts to a predetermined range for each of the rotation positions (e.g., 0°, 90°, or 180°) of the adapter assembly 100 in relation to the handle assembly 20. For example, the distance traveled by the motor shafts may have to be within a predetermined range based on the ratiometric relationship of the gear ratios.

Next, at step 414, the method determines the rotation positions (e.g., 0°, 90°, or 180°) of the adapter assembly 200 relative to the handle assembly 20 based on the predetermined range for each of the rotation positions. For example, the adapter assembly 200 may be rotated about 93° relative to the handle assembly 20. The predetermined range for the 90° rotation position may be from about 75° to 105°.

Next, at step 418, the method determines if the stapling instrument 10 is in a valid position, i.e., a position in which the tissue gap is in the predetermined range for the determined rotation position (e.g., 0°, 90°, or 180°). The predetermined range for the tissue gap is controlled by the controller 300. In a case where the stapling instrument 10 is not in a valid position ("NO" at step 418), then at step 424, the method determines the percent the patient's tissue is clamped. In a case where the stapling instrument is not in a valid position ("YES" at step 418), then at step 424, the method emits an error tone, and at step 422 the method sends a graphic signal to a display indicating to a clinician an invalid rotation, for example, "ERR INVALID ROTATE."

Next, at step 420, the method determines, based on the position of the respective motor shaft, if the anvil assembly 50 is in a valid position, i.e., is the tissue gap within the predetermined range for the determined rotation position (e.g., 0°, 90°, or 180°). In aspects of the disclosure, the method may determine a rotation compensation value based on a difference between a determined rotation position and the predetermined range. The rotation compensation value is an amount that the motor shafts must be rotated to have the motor shafts in a suitable position for executing the selected function, for example, clamping, stapling, and/or cutting tissue. For example, the method may adjust the drive assembly 114 to adjust the position of the anvil assembly 50 (e.g., approximate the anvil assembly 50) of the stapling instrument 10 to be in a position for proper staple formation. The rotation compensation value is used to recalibrate the surgical instrument 10 to ensure that the proper stroke for each of the drive assemblies 114, 116, 119 is produced upon actuation to properly treat tissue.

If the drive assemblies are not in valid positions, the method may further display a graphic warning on a display indicating an invalid rotation or emit an error tone indicating an invalid rotation.

Persons skilled in the art will appreciate that one or more operations of the method 400 may be performed in a different order, repeated, and/or omitted without departing from the scope of the disclosure. In aspects of the disclosure, the illustrated method 400 can operate in controller 300 (FIG. 3), in a remote device, or in another server or system. Other variations are contemplated to be within the scope of the disclosure. The operations of method 400 will be described with respect to a controller, e.g., controller 300 of the stapling instrument 10 (FIG. 3), but it will be understood that the illustrated operations are applicable to other systems and components thereof as well.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A method for powered surgical stapling instrument rotation adjustment, comprising:
   measuring a change in position of a first motor shaft of the surgical stapling instrument relative to a stored rotation verification position of the first motor shaft resulting from manual rotation of an adapter assembly of the surgical stapling instrument in relation to a handle assembly of the surgical stapling instrument;
   determining a distance traveled by a first drive assembly of the adapter assembly of the surgical stapling instrument resulting from the change in position of the first motor shaft;
   comparing the determined distance traveled to a first stored rotation verification position of the first motor shaft;
   determining if the compared distance falls into a predetermined acceptable range of rotation positions; and
   adjusting the position of the drive shaft if the compared distance is not within the predetermined range.

2. The method of claim 1, further comprising:
   determining a rotation compensation value based on a difference between the predetermined rotation position and the compared distance,
   wherein adjusting the position of the drive shaft is based on the rotation compensation value.

3. The method of claim 2, wherein determining the rotation verification position is based on a predetermined distance to be traveled by the first drive assembly.

4. The method of claim 1, further comprising determining a distance traveled by a second drive assembly.

5. The method of claim 4, wherein the determined distance traveled by the second drive assembly is based on a ratiometric relationship between a first gear ratio of the first drive assembly and a second gear ratio of the second drive assembly of surgical stapling instrument.

6. The method of claim 5, wherein the first gear ratio is related to a first mode of operation of the surgical stapling instrument and the second gear ratio is related to a second mode of operation of the surgical stapling instrument.

7. The method of claim 6, wherein a first mode includes a clamping function.

8. The method of claim 1, wherein in a case where the first drive assembly is not in a valid position, the method further comprises displaying a graphic warning on a display indicating an invalid rotation position.

9. The method of claim 1, wherein in a case where the first drive assembly is not in a valid position, the method further comprises emitting an error tone indicating an invalid rotation position.

10. The method of claim 1, further comprising calculating a percent clamped based on determined distance traveled by the first drive assembly.

11. A surgical circular stapling instrument comprising:
    an adapter assembly including:
       an anvil assembly including an anvil head and an anvil center rod extending proximally from the anvil head;
       a reload assembly including an annular staple cartridge including a plurality of staples, and a staple pusher; and
       a first drive assembly including a first lead screw and a first nut, the first lead screw movable through a predetermined stroke to move the anvil assembly in relation to the staple cartridge;
    a handle assembly including:
       a first motor including a first motor shaft configured to advance the first drive assembly;

a processor; and a memory, including instructions stored thereon, which, when executed, cause the surgical circular stapling instrument to:

measure a change in position of the first motor shaft relative to a stored rotation verification position of the first motor shaft resulting from manual rotation of the adapter assembly of the surgical stapling instrument in relation to a handle assembly of the surgical stapling instrument;

determine a distance traveled by a first drive assembly of the adapter assembly of the surgical stapling instrument resulting from the change in position of the first motor shaft;

compare the determined distance traveled to a first stored rotation verification position of the first motor shaft;

determine if the compared distance falls into a predetermined acceptable range of rotation positions; and adjust the position of the drive shaft if the compared distance is not within the predetermined range.

12. The surgical circular stapling instrument according to claim 11, the instructions, when executed, further cause the surgical stapling instrument to determine a rotation compensation value based on a difference between the predetermined rotation position and the compared distance, wherein adjusting the position of the drive shaft is based on the rotation compensation.

13. The surgical circular stapling instrument according to claim 12, wherein determining the rotation verification position is based on a predetermined distance to be traveled by the first drive assembly.

14. The surgical circular stapling instrument according to claim 11, wherein the adapter assembly further includes a second drive assembly including a second lead screw and a second nut, the second lead screw movable through a predetermined stroke to move the staple pusher in relation to the staple cartridge, wherein the handle assembly further includes a second motor including a second motor shaft, configured to advance the second drive assembly, and wherein the instructions, when executed, further cause the surgical stapling instrument to determine a distance traveled by the second drive assembly.

15. The surgical circular stapling instrument according to claim 14, wherein the determined distance traveled by the second drive assembly is based on a ratiometric relationship between a first gear ratio of the first drive assembly and a second gear ratio of the second drive assembly.

16. The surgical circular stapling instrument according to claim 15, wherein the first gear is related to a first mode and a second gear is related to a second mode of the surgical stapling instrument.

17. The surgical circular stapling instrument according to claim 11, in a case where the first drive assembly is not in a valid position, the instructions, when executed, further cause the surgical stapling instrument to display a graphic warning on a display indicating an invalid rotation.

18. The surgical circular stapling instrument according to claim 11, in a case where the first drive assembly is not in a valid position, the instructions, when executed, further cause the surgical stapling instrument to emit an error tone indicating an invalid rotation.

19. The surgical circular stapling instrument according to claim 11, the instructions, when executed, further cause the surgical stapling instrument to calculate a percent clamped based on the determined distance traveled by the first drive assembly.

20. A non-transitory computer-readable medium storing instructions which, when executed by a processor, cause the processor to perform a method for surgical stapling instrument rotation adjustment, the method comprising:

measuring a change in position of a first motor shaft of the surgical stapling instrument relative to a stored rotation verification position of the first motor shaft resulting from manual rotation of an adapter assembly of the surgical stapling instrument in relation to a handle assembly of the surgical stapling instrument;

determining a distance traveled by a first drive assembly of the adapter assembly of the surgical stapling instrument resulting from the change in position of the first motor shaft;

comparing the determined distance traveled to a first stored rotation verification position of the first motor shaft;

determining if the compared distance falls into a predetermined acceptable range of rotation positions; and adjusting the position of the drive shaft if the compared distance is not within the predetermined range.

* * * * *